(12) United States Patent
Oldenburger et al.

(10) Patent No.: US 11,576,759 B2
(45) Date of Patent: Feb. 14, 2023

(54) DENTAL SHAPED BODIES WITH CONTINUOUS SHADE GRADIENT

(71) Applicant: VOCO GmbH, Cuxhaven (DE)

(72) Inventors: Daniel Oldenburger, Cuxhaven (DE); Marie Appelmann, Cuxhaven (DE); Manfred Thomas Plaumann, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 1017 days.

(21) Appl. No.: 16/277,029

(22) Filed: Feb. 15, 2019

(65) Prior Publication Data

US 2019/0247168 A1    Aug. 15, 2019

(30) Foreign Application Priority Data

Feb. 15, 2018 (DE) .......................... 102018103415.6

(51) Int. Cl.

| A61C 13/08 | (2006.01) |
| A61C 13/00 | (2006.01) |
| A61C 13/087 | (2006.01) |
| A61C 5/77 | (2017.01) |
| A61C 5/73 | (2017.01) |
| A61K 6/78 | (2020.01) |
| A61K 6/818 | (2020.01) |

(52) U.S. Cl.
CPC ............. *A61C 13/082* (2013.01); *A61C 5/77* (2017.02); *A61C 13/0004* (2013.01); *A61C 13/0022* (2013.01); *A61C 13/087* (2013.01); *A61C 5/73* (2017.02); *A61C 13/0006* (2013.01); *A61C 13/081* (2013.01); *A61K 6/78* (2020.01); *A61K 6/818* (2020.01); *Y10T 428/12229* (2015.01)

(58) Field of Classification Search
None
See application file for complete search history.

(56) References Cited

U.S. PATENT DOCUMENTS

| 3,347,954 A | 10/1967 | Bredereck et al. |
| 3,451,924 A | 6/1969 | Helfferich et al. |
| 4,002,669 A | 1/1977 | Gross et al. |
| 4,298,738 A | 11/1981 | Lechtken et al. |
| 4,323,348 A | 4/1982 | Schmitz-Josten et al. |
| 4,447,520 A | 5/1984 | Henne et al. |

(Continued)

FOREIGN PATENT DOCUMENTS

| DE | 758 675 | 5/1953 |
| DE | 2419887 | 11/1974 |

(Continued)

OTHER PUBLICATIONS

Dietschi et al., "A new shading concept based on natural tooth color applied to direct composite restorations", Quintessence Int., Feb. 1, 2006, vol. 37, No. 2, pp. 91-102.

*Primary Examiner* — Elizabeth Collister
(74) *Attorney, Agent, or Firm* — Duane Morris LLP; Gregory M. Lefkowitz; Brandon A. Chan

(57) ABSTRACT

What is described is a milling blank having a continuous shade gradient for production of an indirect dental restoration, composed of resin or a resin-based composite. What is also described is a method of producing such a milling blank by mixing two differently coloured pastes with continuous variation of the mixing ratio of the two pastes during the dispensing operation.

9 Claims, 4 Drawing Sheets

L* value (Example 2)

(56) References Cited

U.S. PATENT DOCUMENTS

| | | |
|---|---|---|
| 4,522,693 A | 6/1985 | Henne et al. |
| 4,744,827 A | 5/1988 | Winkel et al. |
| 4,744,828 A | 5/1988 | Winkel et al. |
| 4,792,632 A | 12/1988 | Ellrich et al. |
| 4,868,091 A | 9/1989 | Boettcher et al. |
| 4,952,614 A | 8/1990 | Reiners et al. |
| 4,970,032 A | 11/1990 | Rotsaert |
| 5,063,257 A | 11/1991 | Akahane et al. |
| 5,100,929 A | 3/1992 | Jochum et al. |
| 5,399,770 A | 3/1995 | Leppard et al. |
| 5,472,991 A | 12/1995 | Schmitt et al. |
| 5,761,169 A | 6/1998 | Mine et al. |
| 5,989,031 A | 11/1999 | Kura et al. |
| 6,020,528 A | 2/2000 | Leppard et al. |
| 6,288,138 B1 | 9/2001 | Yamamoto et al. |
| 6,355,704 B1 | 3/2002 | Nakatsuka et al. |
| 6,365,771 B1 * | 4/2002 | Suzuki et al. ............ G03F 7/27 560/220 |
| 6,379,593 B1 | 4/2002 | Datzmann et al. |
| 6,613,812 B2 | 9/2003 | Bui et al. |
| 7,081,485 B2 | 7/2006 | Suh et al. |
| 7,148,382 B2 | 12/2006 | Wolf et al. |
| 7,214,726 B2 | 5/2007 | Qian |
| 7,601,767 B2 | 10/2009 | Ruppert et al. |
| 7,604,480 B2 | 10/2009 | Grundler et al. |
| 7,879,924 B2 | 2/2011 | Torii et al. |
| 7,981,531 B2 | 7/2011 | Rheinberger et al. |
| 7,989,519 B2 | 8/2011 | Vogt et al. |
| 8,025,992 B2 | 9/2011 | Engels et al. |
| 8,883,876 B2 | 11/2014 | Lueck |
| 9,649,179 B2 | 5/2017 | Jung et al. |
| 9,839,498 B2 | 12/2017 | Goto et al. |
| 2006/0247330 A1 | 11/2006 | Takano et al. |
| 2007/0027229 A1 | 2/2007 | Moszner et al. |
| 2007/0142495 A1 | 6/2007 | Neffgen et al. |
| 2008/0167399 A1 | 7/2008 | Utterodt et al. |
| 2009/0036565 A1 | 2/2009 | Utterodt et al. |
| 2012/0123012 A1 | 5/2012 | Rheinberger et al. |
| 2015/0238291 A1 * | 8/2015 | Hauptmann ............ A61C 13/08 264/16 |
| 2016/0262860 A1 | 9/2016 | Korten et al. |

FOREIGN PATENT DOCUMENTS

| | | |
|---|---|---|
| DE | 3236026 | 3/1984 |
| DE | 19944130 | 4/2001 |
| DE | 1020110055393 | 5/2013 |
| DE | 102017202417 | 11/2017 |
| EP | 0007508 | 2/1980 |
| EP | 0173567 | 5/1986 |
| EP | 0948955 | 10/1999 |
| EP | 1236459 | 4/2002 |
| EP | 1839640 | 10/2007 |
| EP | 1881010 | 1/2008 |
| EP | 2070506 | 6/2009 |
| EP | 2070935 | 6/2009 |
| EP | 2829251 | 1/2015 |
| EP | 2995434 | 3/2016 |
| EP | 3173048 | 5/2017 |
| WO | 0144873 | 6/2001 |
| WO | 0209612 | 2/2002 |
| WO | 02092021 | 11/2002 |
| WO | 02092023 | 11/2002 |
| WO | 2008083358 | 7/2008 |
| WO | 2013156483 | 10/2013 |
| WO | 2015051095 | 4/2015 |

* cited by examiner

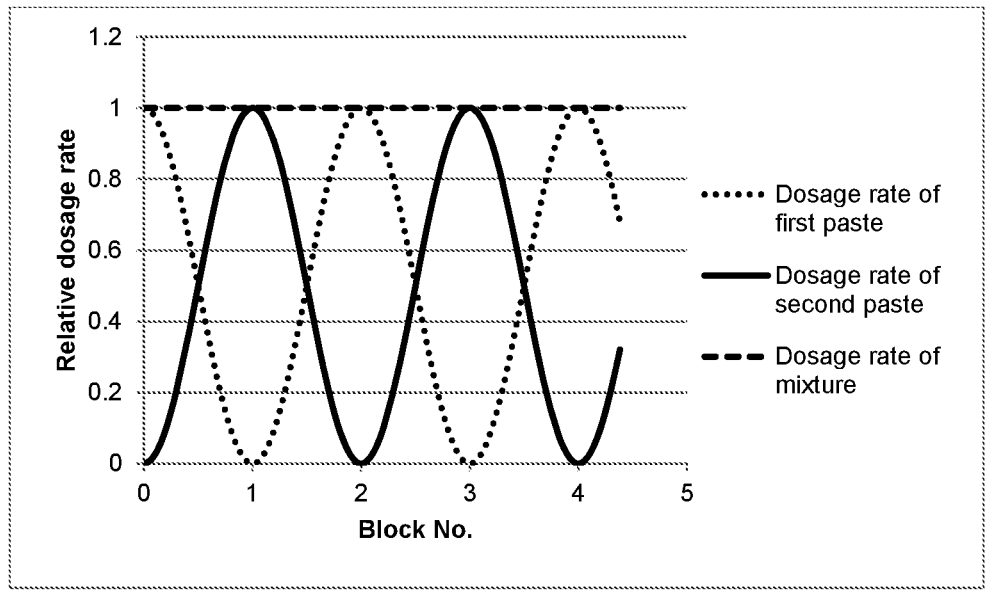
Figure 1: Representation of the dosage rates
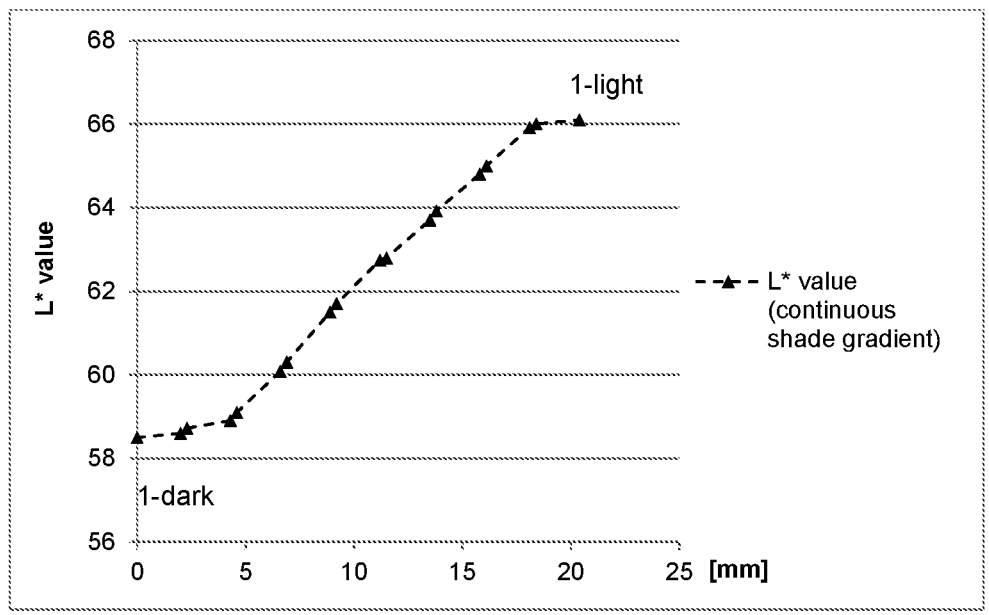
Figure 2: L* value (Example 2)

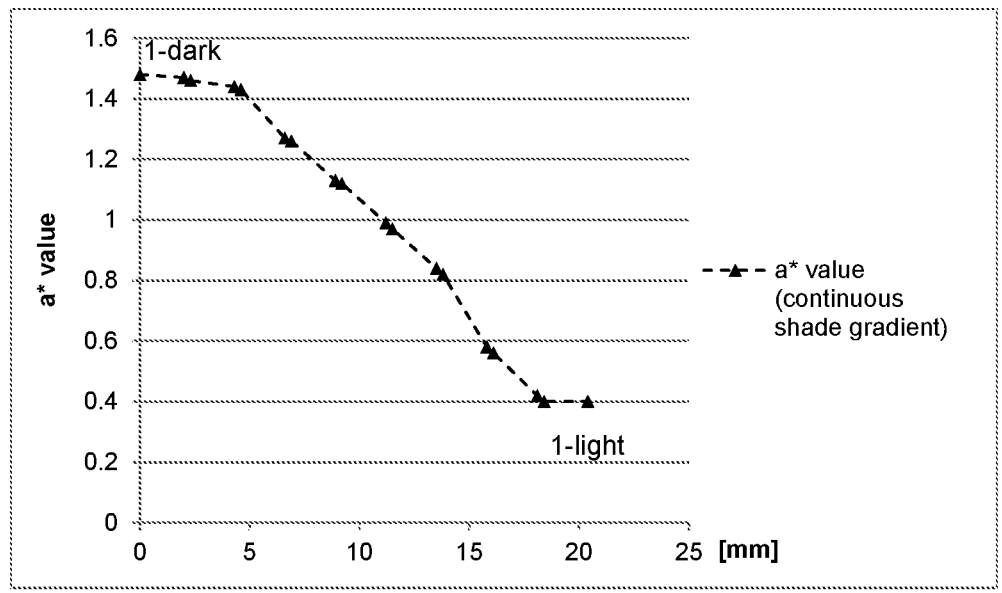
Figure 3: a* value (Example 2)
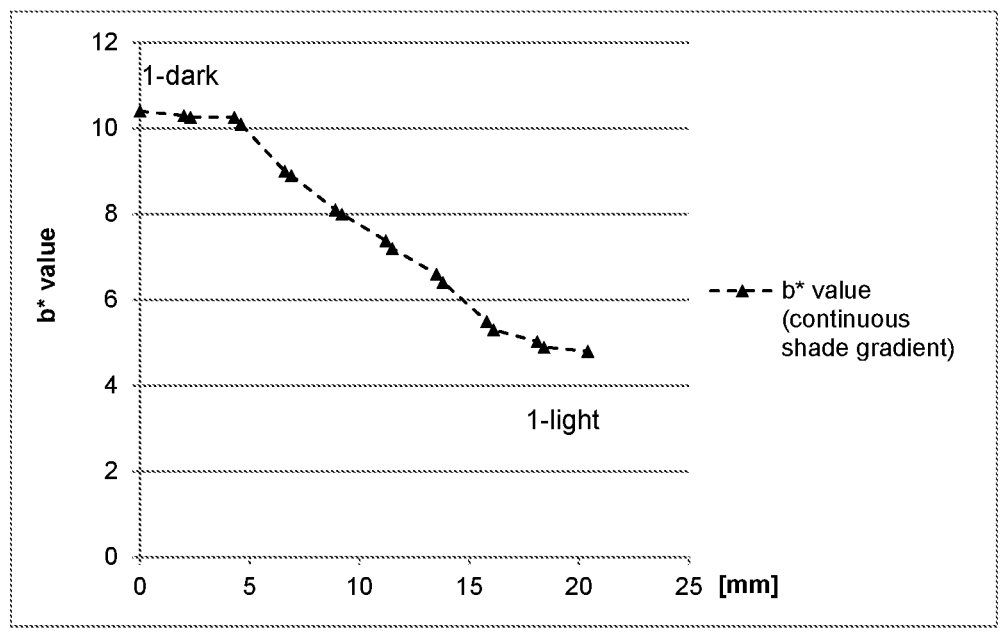
Figure 4: b* value (Example 2)

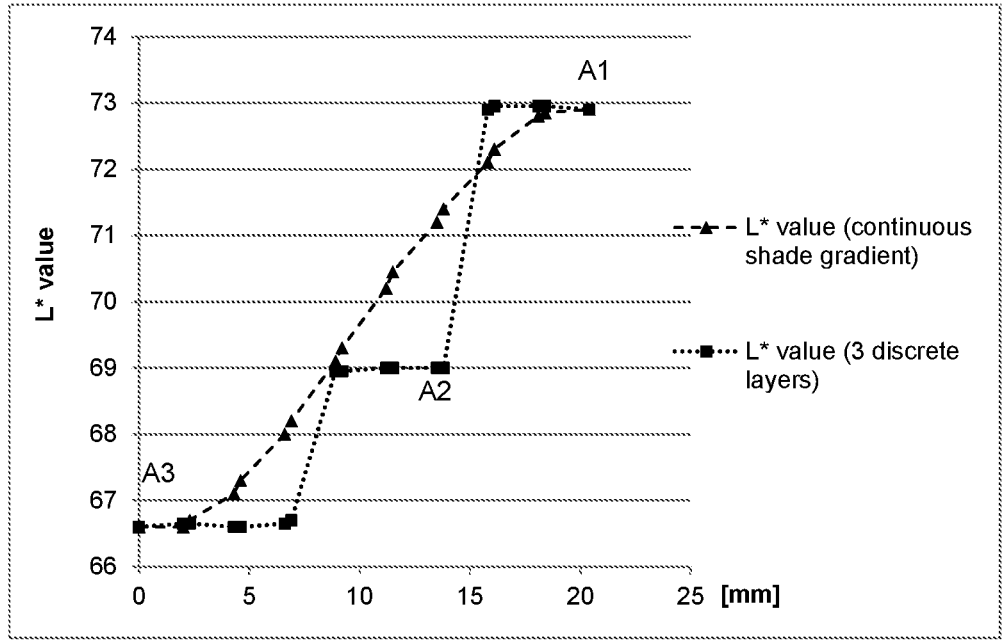
Figure 5: L* value (Example 3)
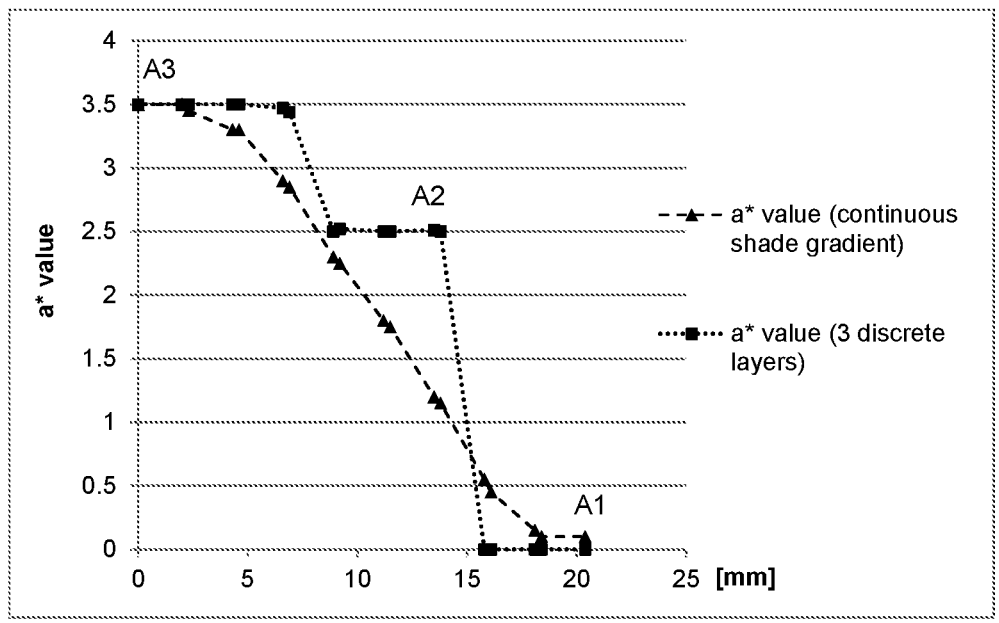
Figure 6: a* value (Example 3)

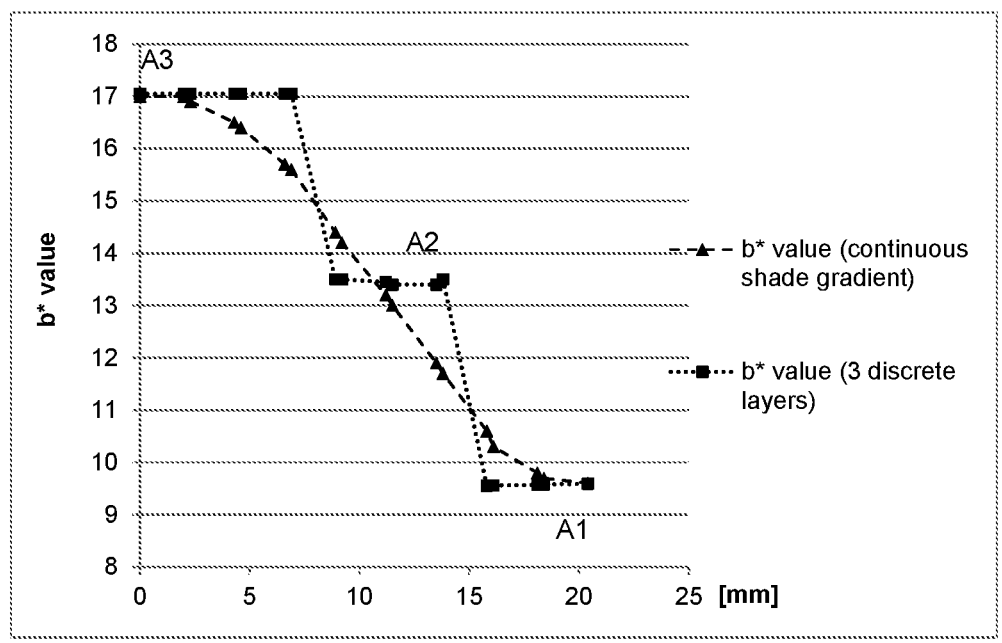
Figure 7: b* value (Example 3)

DENTAL SHAPED BODIES WITH CONTINUOUS SHADE GRADIENT

The present invention relates to multicoloured dental milling blanks based on resin or composite for production of tooth restorations in a CAD/CAM method and to a method of producing these multicoloured dental milling blanks. The present invention further relates to multicoloured artificial teeth based on resin or composite and to a method for producing these multicoloured artificial teeth.

Prosthetics constitute a restoration or replacement for teeth and include, for example, crowns and bridges, partial crowns, inlays, onlays or veneers.

Technical progress in computer-controlled machines resulted in the development of milling machines capable of producing prosthetic restorations with unprecedented accuracy in the shortest time possible and with minimal effort. Against this background, so called "digital dentistry" developed. Today it is of outstanding importance in dentistry, dental technology and medical technology, and thus is in the daily practice and laboratory routine of dental practitioners.

In the beginning, exclusively ceramic or metallic materials were milled, but in view of the dental composite materials that were becoming increasingly better adapted to the natural hard tooth structure, this substance class also became interesting for use as milling blanks.

In contrast to composite materials, which can be adjusted to the manifold requirements on dental material in the hostile environment of the oral cavity by targeted formulation of resin matrix and filler composition, ceramic materials can have excessively high levels of hardness and have a tendency to fracture due to their inherent brittleness. Metallic materials are difficult to adjust aesthetically and often cause allergic reactions in patients.

In addition to good mechanical properties, the demands on the aesthetic properties of prosthetic restorations are increasing. Thus, the natural appearance of the teeth should be reproduced as closely as possible.

Since natural teeth are not monochrome but have a complex shade gradient with changing colour and translucency, restorations made from monochrome milling blanks are incapable of reflecting the natural appearance.

Monochrome restorations can subsequently be individualized with composite characterization colours or individually veneered. These procedures are complex, and time-consuming and costly.

Different multicoloured dental milling blanks have therefore been proposed.

WO 2008/083358 A1 describes dental milling blanks that have different-coloured inner and outer regions.

DE 197 14 178 C2 describes the production of multicoloured, essentially ceramic shaped bodies. Pressing of individual, differently coloured layers is intended to make the colour transitions between the individual layers less perceptible.

DD 758 675 also describes the production of artificial teeth by pressing of different colour layers. For this purpose, differently coloured resins are successively pressed individually.

EP 0 482 000 describes multicoloured resin blocks for production of artificial teeth or crowns. The blocks contain differently coloured, discrete layers.

EP 3 173 048 A1 describes multicoloured resin blocks for production of crowns and bridges. The blocks likewise contain differently coloured, discrete layers.

WO 02/09612 A1 describes multicoloured CAD/CAM blocks composed of composite, resin or ceramic for production of crowns, bridges, inlays and artificial dentition. The blocks likewise contain differently coloured, discrete layers, wherein the lighter, translucent layers are supposed to reproduce the enamel regions, and the darker, more opaque layers the dentine regions.

EP 1 900 341 B1 describes multicoloured, essentially ceramic shaped bodies having layers on top of each other. An opposing shade gradient of main layers and interlayers is intended to make these layers individually imperceptible to the human eye.

EP 2 829 251 A1 and U.S. Pat. No. 9,649,179 B2 describe multicoloured dental milling blanks composed of zirconia. The milling blanks consist of differently coloured layers.

EP 0 772 424 A1 describes multicoloured, multilayer artificial teeth that are produced by injection moulding.

All these known multicoloured dental milling blanks or artificial teeth that consist of differently coloured layers or regions have the disadvantage that the individual discrete layers or regions do not give a natural, continuous shade gradient. Instead, transitions between the individual layers or regions are perceived.

EP 1 859 758 A1 describes the production of ceramic dental block bodies with a continuous shade gradient. Since the production here is carried out using ceramic powders, the production method cannot be transferred to modern resin-based milling blanks.

The objective addressed by the present application was therefore to provide composite-based dental milling blanks with a continuous shade gradient that are capable of reflecting the natural shade gradient of the teeth and can thus be used in CAD/CAM procedures to manufacture aesthetic.

At the same time, the continuous shade gradient should not be adjusted at the expense of the mechanical properties. Instead, the milling blanks should have both a continuous shade gradient and thus an aesthetic appearance as well as good mechanical properties.

According to the invention, the objective is achieved by a milling blank for production of an indirect dental restoration composed of resin or of a resin-based composite, characterized in that the colour changes continuously from one corner to the diametrically opposite corner and/or from one edge to the opposite edge and/or from one face to the opposite face, and especially by a milling blank wherein the L* value and/or the a* value and/or the b* value in the L*a*b* colour space change continuously from one corner to the diametrically opposite corner and/or from one edge to the opposite edge and/or from one face to the opposite face.

According to the invention, the objective is likewise achieved by an artificial tooth composed of resin or composed of a resin-based composite, characterized in that the artificial tooth has a continuous shade gradient from basal to incisal or occlusal and hence corresponds to the natural appearance of a tooth.

It is a feature of a preferred milling blank that the L* value in the L*a*b* colour space changes continuously from a value L*1 at a first corner and/or edge and/or face to a value L*2 in each case at the opposite corner and/or edge and/or face, wherein $$L*2 > L*1,$$

and/or wherein the a* value in the L*a*b* colour space changes continuously from a value a*1 at a first corner and/or edge and/or face to a value a*2 in each case at the opposite corner and/or edge and/or face, wherein $$a*2 < a*1,$$

and/or wherein the b* value in the L*a*b* colour space changes continuously from a value b*1 at a first corner and/or edge and/or face to a value b*2 in each case at the opposite corner and/or edge and/or face, wherein $$b*2<b*1.$$

It is a feature of a preferred milling blank that the difference $\Delta L^* = |L^*2 - L^*1|$ is greater than 2, preferably greater than 4, and/or the difference $\Delta a^* = |a^*1 - a^*2|$ is greater than 0.5, preferably greater than 1 and/or the difference $\Delta b^* = |b^*1 - b^*2|$ is greater than 1, preferably greater than 2.

In a preferred milling blank,

L*1 is in the range from 50 to 70, preferably from 50 to 68,

L*2 is in the range from 65 to 85, preferably from 68 to 85, a*1 is in the range from 3 to 7, preferably from 3.5 to 7, a*2 is in the range from −2 to 4, preferably from −2 to 3.5, b*1 is in the range from 12 to 22, preferably from 14 to 22, and b*2 is in the range from 5 to 15, preferably from 5 to 14.

CAD/CAM blanks are supplied in the form of cubes, cuboids, cylinders or discs.

A milling blank according to the invention has x, y and z dimensions of at least 5 mm, preferably at least 10 mm, more preferably at least 14 mm.

The dimensions of the milling blank are preferably selected such that it can be used to mill a cube having an edge length of 10 mm, preferably 14 mm, and/or a cuboid having a quadratic base area having an edge length of 10 mm, preferably 14 mm, and a height of 20 mm.

It is thus possible to use such a milling blank to produce dental shaped bodies, especially crowns, partial crowns, bridges, inlays, onlays, veneers, partly or fully anatomical artificial teeth or abutments.

In the context of this application, a "continuous shade gradient" is understood to mean that there is no abrupt change in the colour values (L*, a*, b* in the CIE 1976 L*a*b* colour space—DIN EN ISO 11664-4:2011 calorimetry—Part 4: CIE 1976 L*a*b* colour space) within the milling blank (with the dimensions x, y, z). In mathematical terms, the functions L*(x,y,z), a*(x,y,z) and b*(x,y,z) are thus continuous, i.e. they have no discontinuities. By contrast, the colour values in a milling blank from the prior art with multiple discrete, differently coloured layers change abruptly from one layer to the next.

In the context of this application, "diametrically opposite corners" is understood to mean that, in a cube or cuboid, there is a diagonal in space between diametrically opposite corners. The diametrically opposite corner is thus the corner furthest away from the first corner.

In the context of this application, "opposite edges" is understood to mean that, in a cube or cuboid, there is a diagonal face between opposite edges. The opposite edge is thus the edge furthest away from the first edge.

In the context of this application, "opposite faces" is understood to mean that the volume of the milling blank is between opposite faces. In a cube or cuboid, these are parallel faces that do not adjoin each other. In a disc (cylinder), these are the top end and bottom end of the disc.

FIG. 1: Representation of the dosage rate for the co-extrusion of two pastes

FIG. 2: Shade gradient (L* value) for Example 2

FIG. 3: Shade gradient (a* value) for Example 2

FIG. 4: Shade gradient (b* value) for Example 2

FIG. 5: Shade gradient (L* value) for Example 3

FIG. 6: Shade gradient (a* value) for Example 3

FIG. 7: Shade gradient (b* value) for Example 3

Composite-based dental milling blanks can be produced by mixing the individual components and kneading them to give a homogeneous paste. This curable composite paste is dispensed into moulds and cured therein.

The filling is effected here from the bottom of the mould upwards. According to whether there is an edge, corner or face at the bottom, in the course of filling, the mould is thus filled from the corner at the bottom to the opposite corner at the top or from the edge at the bottom to the opposite edge at the top or from the face at the bottom to the opposite face at the top.

A preferred method of producing a milling blank for the production of an indirect dental restoration composed of resin or composed of a resin-based composite comprises the following steps:

producing or providing a first free-radically curable composition having a first colour, producing or providing a second free-radically curable composition having a second colour, filling a mould with mixing of the first and second free-radically curable compositions and curing the mixture of the first and second compositions, wherein the mixing ratio of the first and second free-radically curable compositions is varied continuously in the filling of the mould from one corner to the diametrically opposite corner and/or from one edge to the opposite edge and/or from one face to the opposite face.

By this method, above-described multicoloured milling blanks are preferably produced.

An advantageous method is one wherein the mixing and filling are effected with a conveying or pressing device, preferably with an extrusion device.

Filling is advantageously effected with an extrusion pressure in the range from 20 to 200 bar and/or at an extrusion rate in the range from 0.1 to 100 mm/min, preferably from 1 to 30 mm/min.

Filling is advantageously effected with application of a vacuum, preferably in the range from −0.5 to −1.0 bar. A vacuum of −0.5 bar is understood to mean a reduced pressure of 0.5 bar, such that the residual pressure in this case is 0.5 bar. Accordingly, at a vacuum of −0.85 bar, the reduced pressure is 0.85 bar and the residual pressure 0.15 bar.

It has been found that multicoloured dental milling blanks can be produced by mixing two or more differently coloured composite pastes during the dispensing while altering the rate of dosage of the individual pastes relative to one another.

For example, a first paste can be dosed at a constant rate and a second paste can be mixed in with a constantly increasing dosage rate during the dispensing operation. Alternatively, it is possible to dose a first paste at a constant rate and mix in the second paste with decreasing dosage rate. If there is alternate filling of one mould at a rising dosage rate of the second paste and one mould at a decreasing dosage rate of the second paste, it is possible to alternately produce milling blanks with shade gradient in one direction and the other. This has the advantage that no material need be discarded from the mixer between the individual filling operations or there is no need to change the mixer in order to always commence filling with the same colour. Since the shade gradient is continuous from one side to the other and the blocks are mirror-symmetric, the two blocks are the same thereafter.

It is alternatively possible simultaneously to increase the dosage rate of the first paste and to lower the dosage rate of the second paste, such that the dosage rate of the mixture overall remains constant. This procedure is preferred when the dispensing line results in limits in respect of the pressure range, the individual dosage rates or the dispensing rate. Here too, by a reversal of the individual dosage rates, it is possible to alternately produce blocks with shade gradient in one direction and the other, such that no material need be discarded from the mixer or the mixer need not be changed in the meantime.

FIG. 1 shows a dosage in which the dosage rate of the first paste (dotted line) in the filling of the first mould decreases continuously, while the dosage rate of the second paste (solid line) increases continuously in the course of filling of the first mould. The dosage rate of the mixture (dotted line) remains constant. The first block (range between 0 and 1 on the x axis) thus has a shade gradient in which the colour changes continuously from the colour of the first paste to the colour of the second paste. In the filling of the second mould, conversely, the dosage rate of the first paste (dotted line) is increased continuously and the dosage rate of the second paste (solid line) is decreased continuously. The second block (range between 1 and 2 on the x axis) thus has a correspondingly reversed shade gradient from the colour of the second paste to the colour of the first paste. Advantageously, there is a sinusoidal change in the dosage rate of the individual pastes. Thus, the control of the dosage is simplified and the risk of colour discontinuities at the transition from one block to the next is reduced. In addition, hold times at the start and end of the filling of a mould can be provided, in which the dosage rates of the pastes remain constant.

In principle, this process is also of wonderful suitability for direct production of artificial teeth with continuous shade gradient. For this purpose, a mould that corresponds to the desired partly or fully anatomical tooth shape is selected. This mould is then filled correspondingly with two differently coloured pastes, with continuous variation in the dosage rate of the two pastes relative to one another.

Such a method of producing an artificial tooth composed of resin or composed of a resin-based composite thus comprises the following steps:
  producing or providing a first free-radically curable composition having a first colour,
  producing or providing a second free-radically curable composition having a second colour,
  filling a mould with mixing of the first and second free-radically curable compositions and
  curing the mixture of the first and second compositions,
  wherein the mixing ratio of the first and second free-radically curable compositions is varied continuously in the course of filling.

An artificial tooth produced by this method has a continuous shade gradient from basal to incisal or occlusal and hence corresponds to the natural appearance of a tooth.

In order to achieve the best possible mechanical properties, a maximum filler content is necessary. At the same time, a high filler content, however, results in a higher viscosity. This constitutes a challenge for the mixing and dispensing of such composite pastes.

In order to be able to homogeneously mix and dispense such high-viscosity composite pastes, it is possible to work, for example, with ram extrusion presses, screw extruders or ram extruders. The individual composite pastes are compacted here before they encounter one another in the respective pressure vessels of the dispensing machine (ram extrusion press, twin-ram extrusion press, screw extruder, ram extruder) under vacuum (from −0.5 mbar to −1.0 mbar), so as to minimize inclusions of air. The materials are then extruded through a suitable mixing element. It is possible here either to fill individual moulds successively and then to cure the material in the moulds or to directly and continuously cure the extruded material.

The composite can be cured by photopolymerization and/or thermal polymerization. Pressure can be applied during the curing in order thus to reduce or completely eliminate possible material discontinuities.

There follows a description of a preferred milling blank composed of resin-based composite. The details relating to the composition are analogously applicable to preferred artificial teeth.

Preference is given to a milling blank according to the invention composed of resin-based composite, comprising
  a) an inorganic filler in an amount of at least 70% by weight, preferably at least 80% by weight, based on the total mass of the milling blank,
  and
  b) a resin matrix (polymer matrix).

Preferably, a preferred milling blank according to the invention composed of resin-based composite comprising an inorganic filler in the above-specified amount and a resin matrix is configured such that the inorganic filler a) comprises:
  a1) a glass composition and
  a2) non-aggregated and non-agglomerated silica having an average particle size of not more than 80 nm.

Particularly advantageous in this respect is a milling blank according to the invention wherein the glass composition a1) comprises
  a first glass composition a1a) having a D50 in the range from 0.4 to 1.0 µm, preferably in the range from 0.5 to 0.9 µm,
  and
  a second glass composition a1b) having a D50 in the range from 1.2 to 5.0 µm, preferably in the range from 1.5 to 4.0 µm,
  wherein the mass ratio of a1a) to a1b) is between 1:1.5 and 1:8, preferably between 1:2 and 1:5,
  wherein the mass ratio of a2) to the sum total of a1a) and a1b) is between 1:3 and 1:6,
  wherein the ratio of the D50 of the first glass composition a1a) to the D50 of the second glass composition a1b) is in the range from 1:1.5 to 1:10, preferably 1:2 to 1:5,
  and wherein the D75 of the first glass composition a1a) is less than the D25 of the second glass composition a1b).

In milling blanks according to the invention, composed of resin-based composite and comprising an inorganic filler a) and a resin matrix b), the resin matrix may account for up to 30% by weight, based on the total mass of the milling blank. However, as well as the inorganic filler a) and resin matrix b) constituents, one or more further constituents that are not assigned either to the inorganic filler or to the resin matrix are frequently also provided, for example residues of initiators for the curing and other additives including possible organic fillers.

A preferred milling blank according to the invention consists of a resin-based composite and comprises a) an inorganic filler in an amount of at least 70% by weight, preferably at least 80% by weight, based on the total mass of the milling blank, and b) a resin matrix, wherein the inorganic filler a) comprises:

a1) a glass composition and a2) non-aggregated and non-agglomerated silica having an average particle size of not more than 80 nm, wherein the glass composition a1) comprises a first glass composition a1a) having a D50 in the range from 0.4 to 1.0 µm, preferably in the range from 0.5 to 0.9 µm, and a second glass composition a1b) having a D50 in the range from 1.2 to 5.0 µm, preferably in the range from 1.5 to 4.0 µm, wherein the mass ratio of a1a) to a1b) is between 1:1.5 and 1:8, preferably between 1:2 and 1:5, wherein the mass ratio of a2) to the sum total of a1a) and a1b) is between 1:3 and 1:6, wherein the ratio of the D50 of the first glass composition a1a) to the D50 of the second glass composition a1b) is in the range from 1:1.5 to 1:10, preferably 1:2 to 1:5, and wherein the D75 of the first glass composition a1a) is less than the D25 of the second glass composition a1b).

Preference is given to a milling blank according to the invention which comprises a) an inorganic filler in an amount of at least 70% by weight, preferably at least 80% by weight, based on the total mass of the milling blank, and b) a resin matrix, wherein the resin matrix b) is a polymer of monomers containing difunctional (meth)acrylates, where the proportion by weight of ethoxylated bisphenol A dimethacrylate having an average degree of ethoxylation of 2 to 4 ethoxy groups per molecule is greater than 40% by weight and less than 50% by weight, based on the total mass of the monomers.

Such a milling blank is produced using a monomer mixture comprising difunctional (meth)acrylates, where the proportion by weight of ethoxylated bisphenol A dimethacrylate having an average degree of ethoxylation of 2 to 4 ethoxy groups per molecule in the monomer mixture is greater than 40% by weight and less than 50% by weight, based on the total mass of the monomers. After mixing the monomer mixture, one or more initiators for curing and additives that are optionally present with the required amount of inorganic filler, the monomer mixture is cured by polymerization to give the resin matrix b) in a customary manner, for example by radiation curing (photochemical) and/or by chemical curing (redox reaction) and/or thermally.

There follows a specification of preferred constituents of milling blanks according to the invention or of curable mixtures from which milling blanks according to the invention are producible. Analogously, these constituents are suitable with preference for producing artificial teeth therefrom.

a) Inorganic Fillers:

The milling blank according to the invention comprises inorganic fillers in an amount of at least 70% by weight, preferably at least 80% by weight, based on the total mass of the milling blank, and curable mixtures for production of a milling blank according to the invention accordingly contain inorganic fillers in an amount of at least 70% by weight, preferably of at least 80% by weight, based on the overall composition of the mixture. Inorganic fillers are preferably used as a mixture of various filler fractions; for optimization of the product properties, inorganic fillers are introduced into the formulations in different grain sizes, and they preferably have a multimodal distribution, very preferably a bimodal distribution.

Depending on the requirements of the individual case, preferred inorganic fillers as constituents of milling blanks according to the invention and of corresponding preliminary mixtures are in the form of compact glasses and/or in the form of different silicas in various sizes and conditions (monodisperse, polydisperse).

Suitable inorganic constituents are, for example, amorphous materials based on mixed oxides composed of $SiO_2$, $ZrO_2$ and/or $TiO_2$ and fillers such as quartz glass ceramic or glass powder, barium silicate glasses, barium fluorosilicate glasses, strontium silicate glasses, strontium borosilicate, Li/Al silicate glasses, barium glasses, calcium silicates, sodium aluminium silicates, fluoroaluminum silicate glasses, oxides of aluminium or silicon, zeolites, apatite, zirconium silicates, sparingly soluble metal salts such as barium sulfate or calcium fluoride, and x-ray-opaque fillers such as ytterbium fluoride.

Preferably, a milling blank according to the invention contains barium aluminium borosilicate glasses as a constituent of the filler component a).

For better incorporation into the resin matrix (polymer matrix), the materials mentioned may have been organically surface-modified; this is preferred in many cases. Examples include the surface treatment of inorganic fillers with a silane. A particularly suitable adhesion promoter is methacryloyloxypropyltrimethoxysilane.

Preferably, a milling blank according to the invention contains surface-treated barium aluminium borosilicate glasses, preferably silanized barium aluminium borosilicate glasses, and most preferably methacryloyloxypropyltrimethoxysilane-treated barium aluminium borosilicate glasses.

In milling blanks according to the invention, preferably and depending on the requirements of the individual case, different silicas are used.

Preferably, as set out above in connection with constituent a2), milling blanks according to the invention contain nanoscale silicas, i.e. silica particles having an average particle size of not more than 80 nm. These silicas are preferably non-aggregated and non-agglomerated. The nanoscale silicas are produced in a known manner, for example by flame pyrolysis, plasma methods, gas phase condensation, colloidal techniques, precipitation methods, sol-gel methods, etc.

If the nanoscale silicas are in non-agglomerated and non-aggregated form, they are preferably in monodisperse form. This is particularly preferred. In order to enable good incorporation of the nanoparticles (particles having an average size of not more than 80 nm) into the resin matrix (polymer matrix) of a free-radically curable dental composition for production of a milling blank according to the invention, the surfaces of the nanoscale silicas have preferably been organically surface-modified, meaning that their surfaces have organic structural elements. Mention should be made again by way of example of the surface treatment of the fillers with a silane. A particularly suitable adhesion promoter for the said nanoparticles is methacryloyloxypropyltrimethoxysilane.

A milling blank according to the invention more preferably contains surface-treated, nanoscale, non-agglomerated and non-aggregated silica particles having an average particle size of not more than 80 nm, preferably silanized nanoscale, non-agglomerated and non-aggregated particles having an average particle size of not more than 80 nm, and most preferably methacryloyloxypropyltrimethoxysilane-treated nanoscale, non-agglomerated and non-aggregated silica particles having an average particle size of not more than 80 nm.

Commercially available nanoscale non-agglomerated and non-aggregated silica sols that can preferably be used in production of a milling blank according to the invention are traded, for example, under the "NALCO COLLOIDAL SILICAS" name (Nalco Chemical Co.), the "Ludox colloidal silica" name (Grace) or the "Highlink OG" name (Clariant).

Preferably, the filler component of a milling blank according to the invention comprises a mixture of a2) non-aggregated and non-agglomerated silica having an average particle size of not more than 80 nm and a second filler in the form of microparticles having an average particle size in the range from 0.4 μm to 5 μm. This second filler is preferably the glass composition defined above as component a1) of a milling blank according to the invention. The combination of nanoparticles, i.e. non-aggregated and non-agglomerated silica having an average particle size of not more than 80 nm, with microparticles (preferably microparticles of a glass composition, cf. a1) above) achieves particularly complete and uniform filling of the volume of the milling blank according to the invention.

Within a corresponding milling blank according to the invention, the effect of the microparticles is substantial uniform filling of the volume, where the remaining cavities between the microparticles are at least partly filled by the above-described nanoparticles (component a2)). Microparticles in connection with the present invention are understood to mean particles having an average particle size of 400 nm to 5 μm. The use of glass compositions as microparticles is preferred.

If microparticles (preferably microparticles of a glass composition a1)) are present in the inorganic filler a) of a preferred milling blank according to the invention, these microparticles preferably have a bimodal particle size distribution. Microparticles having a bimodal particle size distribution are preferred since more complete filling of volume is achievable therewith than in the case of use of microparticles having a monomodal particle size distribution. In the case of presence of a bimodal particle size distribution, the particles in the fractions having the greater particle size bring about coarse filling of the volume, while the particles of the fraction having the smaller particle size, as far as possible, fill the regions between the particles of the fractions having the greater particle size. The voids that then still remain are filled by nanoparticles as described above.

Preference is given to use of a mixture of two microparticle fractions, where a first microparticle fraction has a D50 in the range from 0.4 to 1.0 μm, preferably in the range from 0.5 to 0.9 μm. This is preferably a first glass composition a1a) (see above for preferred configurations). The second microparticle fraction has a D50 in the range from 1.2 μm to 5.0 μm, preferably in the range from 1.5 μm to 4.0 μm. This is preferably a second glass composition a1b) as defined above (see above for preferred configurations).

Preferably, the ratio of the total mass of such a first microparticle fraction to the total mass of such a second microparticle fraction is in the range from 1:1.5 to 1:8, preferably in the range from 1:2 to 1:5. This applies in particular if the first microparticle fraction is a first glass composition a1a) and the second microparticle fraction is a second glass composition a1b).

b) Resin Matrix (Polymer Matrix) and Monomers for Production of Such a Resin Matrix:

A milling blank according to the invention for production of an indirect dental restoration consisting of resin or a resin-based composite. For production of the cured resin or of the resin matrix (polymer matrix, which makes up the polymer component in the resin-based composite), free-radically polymerizable monomers are used as a constituent of a free-radically curable composition which additionally also contains inorganic filler of component a) and optionally further components. The proportion of the polymer of the free-radically polymerizable monomers in a milling blank according to the invention is preferably not higher than 30% by weight, since an inorganic filler is preferably present in an amount of at least 70% by weight (see above). The same applies for the free-radically curable composition in which the free-radically polymerizable monomers are used along with fillers.

The free-radically polymerizable monomers are preferably the (meth)acrylate monomers customarily used in composite materials in dental chemistry. A corresponding polymer then comprises a corresponding poly(meth)acrylate. In the context of this application, (meth)acrylates are understood to mean both methacrylates and acrylates.

The patent literature mentions a multitude of compounds (for example document DE 39 41 629 A1) that are all diesters of acrylic acid or methacrylic acid and are suitable for production of a resin or of a resin matrix of a resin-based composite as present in a milling blank according to the invention.

In a preferred embodiment of a milling blank according to the invention, this milling blank comprises a resin matrix which is produced by polymerization of one or more monomers selected from the group consisting of ethylene glycol dimethacrylate (EGDMA), hexane-1,6-diol dimethacrylate (HDDMA), triethylene glycol dimethacrylate (TEGDMA), decane-1,10-diol dimethacrylate (DEDMA), dodecane-1,12-diol dimethacrylate (DODMA), ethoxylated bisphenol A dimethacrylate, ethoxylated bisphenol A dimethacrylate wherein the bisphenol is reacted with 2 to 4 mol of ethylene oxide and then the intermediate is saturated with 2 mol of methacrylic acid, polyethylene glycol dimethacrylate (PEGDMA), 7,7,9-trimethyl-4,13-dioxo-3,14-dioxa-5,12-diazahexadecane 1,16-dioxydimethacrylate (UDMA), butanediol dimethacrylate, tetraethylene glycol dimethacrylate, neopentyl glycol dimethacrylate and bisphenol A glycidyl methacrylate (bis-GMA).

Preference is given in the specific case to the corresponding dimethacrylates or diacrylates of dihydroxymethyltricyclo[5.2.1.0$^{2,6}$]decane, as described in documents DE 1816823, DE 2419887, DE 2406557, DE 2931926, DE 3522005, DE 3522006, DE 3703120, DE 102005021332, DE 102005053775, DE 102006060983, DE 69935794 and DE 102007034457.

c) Initiators:

Preferred milling blanks according to the invention are producible by radiation curing (photochemically) and/or by chemical curing (redox reactions) and/or thermally by curing a corresponding composition, wherein the composition contains, as component a), an inorganic filler in an amount of at least 70% by weight, preferably at least 80% by weight, based on the total mass of the milling blank produced and/or of the compositions used, or is a filler-free composition for production of a milling blank from resin. For production of a milling blank, preference is given in accordance with the invention to the thermal curing of a corresponding composition, the thermal curing being initiated, for example, by peroxide decay.

Examples of suitable photosensitizers are alpha-diketones, benzoin alkyl ethers, thioxanthones, benzophenones, acylphosphine oxides, acylgermanium compounds, acetophenones, ketals, titanocenes, sensitizing dyes, etc. The sensitizers can be employed alone or in combination. Specific substance examples from the different classes can be found, for example, in DE 10 2006 019 092 A1, or in DE 39 41 629 C2.

Examples of accelerators which are used together with the sensitizers are tertiary amines, secondary amines, barbituric acids, tin compounds, aldehydes and sulfur compounds. Specific substance examples from the different classes can be found in DE 10 2006 019 092 or in DE 39 41 629 C2.

Further suitable initiators and initiator combinations are described in DE 601 16 142.

Suitable photoinitiators are characterized in that they can initiate the curing of a free-radically curable dental composition by absorption of light within the wavelength range from 300 nm to 700 nm, preferably from 350 nm to 600 nm and more preferably from 380 nm to 500 nm, optionally in combination with one or more co-initiators.

The absorption maximum of camphorquinone (CQ) is at about 470 nm and is therefore within the blue light range. Camphorquinone (CQ) is one of the $PI_2$ initiators and is regularly used together with a co-initiator.

A suitable catalyst system contains the combination of an alpha-diketone and an aromatic tertiary amine, preference being given to the combination of camphorquinone (CQ) and ethyl p-N,N-dimethylaminobenzoate (DABE).

Likewise preferable is the further combination of the "alpha-diketone/aromatic tertiary amine" system with a phosphine oxide, especially with phenyl bis(2,4,6-trimethylbenzoyl)phosphine oxide and/or 2,4,6-trimethylbenzoyldiphenylphosphine oxide. With regard to the structures of suitable phosphine oxides, reference is made to publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2.

The phosphine oxides specified in these publications are suitable particularly alone or in combination with the "alpha-diketone/amine" system as photopolymerization initiator system.

Further suitable photoinitiators are described in J.-P. Fouassier, Photoinitiation, Photopolymerization and Photocuring, Hanser Publishers, Munich, Vienna, New York 1995, and in J. F. Rabek (ed.), Radiation Curing in Polymer Science and Technology, Vol. II, Elsevier Applied Science, London, N.Y. 1993.

The person skilled in the art is aware of various initiators for chemical curing. In this context, reference is made by way of example to EP 1 720 506. Initiators for chemical curing are also described in the already above-mentioned documents DE 10 2006 019 092 and DE 39 41 629.

Preferred initiators for chemical curing are dibenzoyl peroxide and dilauroyl peroxide, especially dibenzoyl peroxide in combination with amines such as N,N-dimethyl-p-toluidine, N,N-dihydroxyethyl-p-toluidine and structurally related amines.

Dual-curing systems comprise a combination of photoinitiators and initiators for chemical curing.

In addition to the oxidative organic peroxide compounds, barbituric acids or barbituric acid derivatives and malonylsulfamides can also be used as redox systems.

Among the barbituric acid systems, "Bredereck systems" are of major importance. Examples of suitable "Bredereck systems" and references to the relevant patent literature can be found in EP 1 839 640 and in DE 1495520, WO 02/092021 or WO 02/092023.

Rather the barbituric acids, the salts thereof can also be used. Examples thereof are found in the following documents: EP 1 872 767, EP 2 070 506, EP 1 881 010, DE 10 2007 050 763, U.S. Pat. No. 6,288,138, DE 11 2006 001 049, U.S. Pat. No. 7,214,726 and EP 2 070 935.

Suitable malonylsulfamides are described in EP 0 059 451. Preferred compounds here are 2,6-dimethyl-4-isobutylmalonylsulfamide, 2,6-diisobutyl-4-propylmalonylsulfamide, 2,6-dibutyl-4-propylmalonylsulfamide, 2,6-dimethyl-4-ethylmalonylsulfamide and 2,6-dioctyl-4-isobutylmalonylsulfamide.

It is also possible to use sulfur compounds in the +2 or +4 oxidation state, such as sodium benzenesulfinate or sodium p-toluenesulfinate.

In order to accelerate curing, the polymerization can be conducted in the presence of heavy metal compounds such as Ce, Fe, Cu, Mn, Co, Sn or Zn, particular preference being given to copper compounds. The heavy metal compounds are preferably used in the form of soluble organic compounds. Preferred copper compounds here are copper benzoate, copper acetate, copper ethylhexanoate, copper di(methacrylate), copper acetylacetonate and copper naphthenate.

If the peroxides are heated, they decompose and form free radicals which are capable of initiating polymerization. The most commonly used system for thermal polymerization is the use of dibenzoyl peroxide. Further thermal initiators are ketone peroxides, peroxy ketals, hydroperoxides, dialkyl peroxides, diacyl peroxides, peroxy esters and peroxydicarbonates such as dicumyl peroxide, chlorobenzoyl peroxide, t-butyl perbenzoate, dilauroyl peroxide, cumene hydroperoxide, tert-butyl 3,5,5-trimethylperoxyhexanoate, and azo compounds such as 2,2'-azobisisobutyronitrile, 2,2'-azobis-2,4-dimethylvaleronitrile, 2,2'-azobis-1-cyclohexanecarbonitrile or dimethyl-2-2'-azobisisobutyrate. Substances such as sodium or potassium persulfate also thermally decompose and are suitable compounds in this connection. These substances can be used individually or in mixtures with one another. For this purpose, the free-radically curable dental compositions merely have to be heated to the decomposition temperature of the respective peroxides indicated by the manufacturer. The free-radically curable compositions are advantageously heated to a temperature above the decomposition temperature and kept at said temperature for a while so that the polymer has the time required for relaxation. The person skilled in the art determines the optimum temperature by successively increasing the temperature for curing up to the point at which the polymer no longer shows any substantial improvements in its important measured parameters, such as flexural strength, modulus of elasticity and water uptake.

Preferably, the thermal curing is performed in such a way that the free-radically curable composition is transferred into a block mould, where it is cured at temperatures of 80° C. to 150° C. and a pressure of 100 to 300 bar.

d) Additives:

In some cases, a milling blank according to the invention comprises one or a plurality of further additive(s).

These additives can have various functions. Customary additives for use in dental materials are known to the person skilled in the art, who will select the suitable additive(s) depending on the function desired. In the following, typical additives and their functions are described by way of example.

UV absorbers which, for example by virtue of their conjugated double bonding systems and aromatic rings, are capable of absorbing UV radiation are in some cases components of a milling blank according to the invention. Examples of UV absorbers are 2-hydroxy-4-methoxybenzophenone, phenyl salicylate, 3-(2'-hydroxy-5'-methylphenyl)benzotriazole and diethyl 2,5-dihydroxyterephthalate. The polymers contain these additives in order to ensure their colour stability.

Since indirect dental restorations are intended to restore teeth as close to nature as possible, it is necessary to provide the milling blanks according to the invention in different shades. For this purpose, as a rule, milling blanks according to the invention contain inorganic dyes and/or organic pigments, preferably in amounts that are very small but sufficient for the purposes mentioned. Typical inorganic pigments are, for example, iron oxides and titanium dioxide. Colourants are listed in an international official list which is published by the Society of Dyers and Colourists in Bradford, England. The generic name is followed by the Colour Index CI.

EXAMPLES

Abbreviations bis-EMA2,6: ethoxylated bisphenol A dimethacrylate having an average of 2.6 ethylene oxide units
bis-GMA: bisphenol A glycidyl methacrylate
TCDDMA: bis(methacryloyloxymethyl)tricyclo[$5.2.1.0^{2,6}$]decane
UDMA: 7,7,9-trimethyl-4,13-dioxo-3,14-dioxa-5,12-diazahexadecane 1,16-dioxydimethacrylate
HDDMA: hexane-1,6-diol dimethacrylate
Dental glass 1: barium aluminium borosilicate glass (D50 0.8 μm/D25 0.5 μm/D75 1.0 μm), silanized
Dental glass 2: barium aluminium borosilicate glass (D50 2.7 μm/D25 1.4 μm/D75 6.1 μm), silanized
Nano-$SiO_2$: non-agglomerated, non-aggregated silica (D50 40 nm), silanized
BPO: dibenzoyl peroxide Colorimetry: For the measurement of the colour values, the composite blocks were sawn parallel to the base into discs of 2 mm thickness with a precision saw (IsoMet 4000, Buehler, circular saw thickness 0.3 mm). A ColorFlex EZ colorimeter (CLFX EZ 45/0 LAV, HunterLab—D65 illuminant, 10° observer ASTM E308) was used in each case to determine the CIE 1976 L*a*b*colour values for the front and reverse side of each disc against a white background (X:79.76, Y:84.89, Z:91.85—D65 illuminant, 10° observer ASTM E308). For the multicoloured composite blocks, a shade gradient is thus found across the overall block. For the single-coloured comparative blocks, only one 2 mm-thick disc was sawn out of the middle of the block and the CIE 1976 L*a*b*colour values were determined thereon against a white background.

Biaxial flexural strength (BFS): Biaxial flexural strength was determined analogously to DIN EN ISO 6872:2009 (7.3.3). For this purpose, first of all, in a 5-axis milling machine (250i, imes-icore GmbH), cylinders having a diameter of 14 mm were ground out of the composite blocks. From these cylinders, a precision saw (IsoMet 4000, Buehler) was then used to produce discs having a thickness of 1.2 mm, which were deburred, ground and polished. The specimens were loaded with a traverse velocity of 1 mm/min until fracture and the biaxial flexural strength was calculated according to the formula given under 7.3.3.4. A value of 0.25 was used as Poisson's ratio.

3-point flexural strength (3PFS): Flexural strength was determined analogously to DIN EN ISO 6872:2009 (7.3.2) with a support width of 12 mm and a roll contact diameter of 2 mm. For this purpose, specimens having a width of 4 mm, a thickness of 1.2 mm and a length of 18 mm were produced from the composite blocks with a precision saw (IsoMet 4000, Buehler), deburred, ground and polished. The samples were loaded with a traverse velocity of 1 mm/min until fracture and the 3-point flexural strength was calculated according to the formula given under 7.3.2.4.1.

Modulus of elasticity: Modulus of elasticity was ascertained analogously to the calculation in ADA Specification No. 27-1993 (7.8.4.2) as the slope of the stress/strain curve from the 3-point flexural strength measurement (see above) in the linear elastic region.

Particle size determination: The particle size of the "nano-$SiO_2$" nanoparticles was determined by means of dynamic light scattering (DLS) with an instrument of the Zetasizer Nano ZS type (Malvern) at 0.5% by weight in 2-butanone (weight by volume). The particle size of the microparticles (dental glass) was determined by means of laser diffraction using an instrument of the Beckmann Coulter LS 13320 type.

Example 1 (Production of the Uncoloured Composite Pastes)

For the production of the uncoloured composite pastes, the individual components were weighed out in accordance with the proportions specified in Table 1 and homogenized in a laboratory kneader (PC Laborsystem, Magden CH) at 50 rpm for 30 minutes. For colouring, small amounts of white, yellow, red, brown and black colour pigments were added to the uncoloured pastes. The person skilled in the art is aware from the colouring of direct composite-based filling materials of the colour pigments and the proportions thereof that have to be selected to obtain a colour that has the desired colour values and corresponds, for example, to a VITA colour. The coloured pastes were homogenized again on a laboratory kneader at 50 rpm for 30 minutes and then degassed at 50 rpm and −0.85 bar for 15 minutes.

TABLE 1

| (parts by weight): | | | | |
|---|---|---|---|---|
| Uncoloured composite paste | | | 1 | 2 |
| Filler (a) | (a1a) | Dental glass 1 | 11.00 | 12.00 |
| | (a1b) | Dental glass 2 | 51.00 | 56.00 |
| | (a2) | Nano-$SiO_2$ (40 nm) | 18.00 | 12.00 |
| | Total (a) | | 80.00 | 80.00 |
| Monomers (b) | (b1a) | Bis-EMA2,6 | 8.00 | 9.00 |
| | (b2) | Bis-GMA | 3.50 | |
| | | TCDDMA | 3.50 | 5.00 |
| | | UDMA | 3.50 | 5.00 |
| | | HDDMA | 1.20 | 0.70 |
| | Total (b) | | 19.70 | 19.70 |
| Initiators (c) | | BPO | 0.30 | 0.30 |
| | Total | | 100.00 | 100.00 |

Example 2

The uncoloured composite paste 1 was coloured differently in two experiments, such that the two pastes are of distinctly different colour (1-light paste and 1-dark paste).

The composite pastes 1-light and 1-dark were each introduced into moulds (base area: 15 mm×15 mm, height 21 mm) by extrusion at a pressure of 100 bar and a vacuum of −0.85 bar.

For the production of the blocks according to the invention, the composite pastes 1-light and 1-dark were introduced into moulds (base area: 15 mm×15 mm, height 21 mm) by co-extrusion at a reduced pressure of −0.85 bar. First of all, 1-dark paste was dosed at 20 mm/min and 1-light paste at 0 mm/min for nine seconds through a static mixer. Subsequently, over a period of 45 seconds, the dosage rate of 1-light paste was increased continuously from 0 to 20 mm/min, while the dosage rate of 1-dark paste was simultaneously lowered continuously from 20 to 0 mm/min. Finally, 1-light paste was dosed at 20 mm/min for another nine seconds (1-dark paste 0 mm/min).

For all blocks, curing was effected under isostatic conditions at 250 bar and with the following temperature programme (20° C.-2° C./min-120° C. (30 min)-5° C./min-20° C.).

The two monochrome comparative blocks have the L*a*b* colour values specified in Table 2. For the block according to the invention with continuous shade gradient, the L*a*b* colour values are shown in FIGS. 2 to 4.

TABLE 2

(colour values of monochrome blocks made from the 1-light and 1-dark pastes):

|  | 1-light | 1-dark |
| --- | --- | --- |
| L* value | 66.1 | 58.5 |
| a* value | 0.4 | 1.5 |
| b* value | 4.8 | 10.4 |

TABLE 3

(flexural strengths):

|  | 1-light | 1-dark | Block with continuous shade gradient |
| --- | --- | --- | --- |
| BFS | 207 MPa | 201 MPa | 206 MPa |
| 3PFS | 181 MPa | 179 MPa | 181 MPa |
| Modulus of elasticity | 13.5 GPa | 13.4 GPa | 13.5 GPa |

Example 3

The uncoloured composite paste 2 was coloured in three different experiments such that it corresponded roughly to VITA colours A1 (Paste 2-A1), A2 (Paste 2-A2) and A3 (Paste 2-A3).

Composite pastes 2-A1, 2-A2 and 2-A3 were each introduced into moulds (base area: 15 mm×15 mm, height 21 mm) by extrusion at a pressure of 100 bar and a reduced pressure of −0.85 bar.

In addition, a mould (base area 15 mm×15 mm, height 21 mm) was filled with three successive layers, each of thickness 7 mm, of the individual pastes 2-A1, 2-A2 and 2-A3.

For the production of the blocks according to the invention, the composite pastes 2-A1 and 2-A3 were introduced into moulds (base area: 15 mm×15 mm, height 21 mm) by coextrusion at a reduced pressure of −0.85 bar. First of all, paste 2-A1 was dosed at 0 mm/min and paste 2-A3 at 10 mm/min for nine seconds through a static mixer. Subsequently, over a period of 108 seconds, the dosage rate of paste 2-A1 was increased continuously from 0 to 10 mm/min, while the dosage rate of paste 2-A3 was simultaneously lowered continuously from 10 to 0 mm/min. Finally, paste 2-A1 was dosed at 10 mm/min for another nine seconds (paste 2-A3 0 mm/min).

For all blocks, curing was effected under isostatic conditions at 250 bar and with the following temperature programme (20° C.-2° C./min-120° C. (30 min)-5° C./min-20° C.).

The three monochrome comparative blocks have the following L*a*b* colour values:

TABLE 4

(colour values of monochrome blocks made from pastes 2-A1, 2-A2 and 2-A3):

|  | 2-A1 | 2-A2 | 2-A3 |
| --- | --- | --- | --- |
| L* value | 73.0 | 69.0 | 66.6 |
| a* value | 0.0 | 2.5 | 3.5 |
| b* value | 9.5 | 13.5 | 17.0 |

The comparative block consists of three discrete layers. The L*a*b* values of the individual layers each correspond to the L*a*b* values of the three individual pastes 2-A1, 2-A2 and 2-A3. From one layer to another, the L*a*b* values change abruptly (cf. FIGS. 5 to 7). The individual layers are visually clearly distinguishable from one another.

By contrast, by dosage of two differently coloured pastes with varying dosage rate, a block in which the L*a*b* values change continuously is obtained (cf. FIGS. 5 to 7). In this block, no discontinuities of colour are visually detectable.

TABLE 5

(flexural strengths):

|  | 2-A1 | 2-A2 | 2-A3 | Block with 3 discrete layers | Block with continuous shade gradient |
| --- | --- | --- | --- | --- | --- |
| BFS | 201 MPa | 197 MPa | 198 MPa | 186 MPa | 200 MPa |
| 3PFS | 177 MPa | 179 MPa | 177 MPa | 175 MPa* | 179 MPa |
| Modulus of elasticity | 13.2 GPa | 13.2 GPa | 13.2 GPa | 13.1 GPa* | 13.2 GPa |

*2 of 10 specimens failed prematurely at the interface between two colours and were not included in the calculation of the averages.

The invention claimed is:

1. A milling blank for the production of an indirect dental restoration composed of resin or of a resin-based composite, characterized in that the colour changes continuously from one corner to the diametrically opposite corner and/or from one edge to the opposite edge and/or from one face to the opposite face.

2. The milling blank according to claim 1, wherein an L* value and/or an a* value and/or a b* value in the L*a*b* colour space change continuously from one corner to the diametrically opposite corner and/or from one edge to the opposite edge and/or from one face to the opposite face.

3. The milling blank according to claim 1, wherein the L* value in the L*a*b* colour space changes continuously from a value L*1 at a first corner and/or edge and/or face to a value L*2 in each case at the opposite corner and/or edge and/or face, wherein L*2>L*1, and/or wherein the a* value in the L*a*b* colour space changes continuously from a value a*1 at a first corner and/or edge and/or face to a value a*2 in each case at the opposite corner and/or edge and/or face, wherein a*2<a*1, and/or wherein the b* value in the L*a*b* colour space changes continuously from a value b*1 at a first corner and/or edge and/or face to a value b*2 in each case at the opposite corner and/or edge and/or face, wherein b*2<b*1.

4. The milling blank according to claim 3, wherein a difference ΔL*=|L*2−L*1| is greater than 2, and/or a difference Δa*=|a*1−a*2| is greater than 0.5, and/or a difference Δb*=|b*1−b*2| is greater than 1, wherein the L*a*b* values are measured on 2 mm-thick discs against a white background.

5. The milling blank according to claim 3, wherein

L*1 is in the range from 50 to 70,

L*2 is in the range from 65 to 85, a*1 is in the range from 3 to 7, a*2 is in the range from −2 to 4, b*1 is in the range from 12 to 22, and b*2 is in the range from 5 to 15, wherein the L*a*b* values are measured on 2 mm-thick discs against a white background.

6. The milling blank according to claim 1, having x, y and z dimensions of at least 5 mm.

7. The milling blank according to claim 1, the dimensions of which are selected such that it can be used for milling of a cube having an edge length of 10 mm, and/or a cuboid having a square base area having an edge length of 10 mm, and a height of 20 mm.

8. Dental shaped body produced from a milling blank according to claim 1.

9. Dental moulding according to claim 8, which is a crown, a partial crown, a bridge, an inlay, an onlay, a veneer, a partly or fully anatomical artificial tooth or an abutment.

* * * * *